United States Patent
Durack et al.

(10) Patent No.: US 9,408,984 B2
(45) Date of Patent: Aug. 9, 2016

(54) SELF-INJECTION DEVICE

(75) Inventors: David T. Durack, Durham, NC (US); Artis R. Lockhart, Durham, NC (US); Lawrence A. Monahan, Willow Springs, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 267 days.

(21) Appl. No.: 13/261,212

(22) PCT Filed: Sep. 15, 2009

(86) PCT No.: PCT/US2009/005148
§ 371 (c)(1),
(2), (4) Date: May 25, 2012

(87) PCT Pub. No.: WO2011/034516
PCT Pub. Date: Mar. 24, 2011

(65) Prior Publication Data
US 2012/0245558 A1    Sep. 27, 2012

(51) Int. Cl.
*A61M 5/32*    (2006.01)
*A61M 5/28*    (2006.01)
*A61M 5/46*    (2006.01)

(52) U.S. Cl.
CPC ............... *A61M 5/326* (2013.01); *A61M 5/282* (2013.01); *A61M 5/46* (2013.01); *A61M 5/3287* (2013.01); *A61M 2005/3247* (2013.01); *A61M 2005/3267* (2013.01)

(58) Field of Classification Search
CPC ................ A61M 5/282; A61M 5/46; A61M 2005/3267; A61M 5/31578; A61M 5/3158; A61M 5/3202; A61M 5/321; A61M 5/3243; A61M 5/3245; A61M 2005/3247; A61M 5/3257; A61M 5/326; A61M 2005/3264; A61M 5/3287; A61M 2005/14252; A61M 2005/14284; A61M 2005/1585

USPC .......... 604/110, 185, 187, 192, 197, 198, 117
See application file for complete search history.

(56) References Cited

U.S. PATENT DOCUMENTS 1,288,174 A    12/1918    Pittenger
2,667,165 A    1/1954    Smith (Continued)

FOREIGN PATENT DOCUMENTS

EP    0258073    6/1987
EP    0 749 758 A1    12/1996

(Continued)

OTHER PUBLICATIONS

Japanese Office Action dated Aug. 20, 2013 issued by the Japanese Patent Office in counterpart Japanese Application No. 2012-529720.

(Continued)

*Primary Examiner* — Aarti B Berdichevsky
*Assistant Examiner* — Laura Schell
(74) *Attorney, Agent, or Firm* — Dickinson Wright PLLC (57) ABSTRACT

A self-injection device (101) for delivering a medicament includes a housing (111), and a needle (103) connected to the housing (111). A compressible reservoir (121) is connected to the housing (111) and is in fluid communication with a needle (103) such that compressing the reservoir (121) delivers medicament from the reservoir (121) to the needle (103) and moves the needle (103) from the first position to the second position. A platform (171) is disposed within the housing (111) about which the housing (111) is rotatable between a plurality of positions. Each of the positions corresponds to a different distance the needle (103) is moved to the second position during an injection to provide a variable injection depth. The needle (103) is withdrawn into the housing (111) after an injection without requiring manual manipulation by the user, thereby preventing needle sticks and other accidents.

20 Claims, 6 Drawing Sheets

(56) References Cited

U.S. PATENT DOCUMENTS

| | | | |
|---|---|---|---|
| 2,874,694 A | | 2/1959 | Blackman |
| 4,282,986 A | | 8/1981 | af Ekenstam |
| 4,522,622 A | | 6/1985 | Peery |
| 4,548,601 A | | 10/1985 | Lary |
| 4,883,473 A | | 11/1989 | Thomas |
| 4,886,499 A | | 12/1989 | Cirelli |
| 4,894,054 A | * | 1/1990 | Miskinyar ............... 604/136 |
| 4,955,871 A | | 9/1990 | Thomas |
| 5,019,048 A | | 5/1991 | Margolin |
| 5,248,303 A | | 9/1993 | Margolin |
| 5,478,315 A | * | 12/1995 | Brothers et al. ............... 604/115 |
| 5,527,287 A | * | 6/1996 | Miskinyar ............... 604/135 |
| 5,860,957 A | * | 1/1999 | Jacobsen ............... A61N 1/30 604/140 |
| 5,944,700 A | | 8/1999 | Nguyen |
| 6,086,562 A | * | 7/2000 | Jacobsen et al. ............... 604/156 |
| 7,252,651 B2 | | 8/2007 | Haider |
| 7,297,136 B2 | * | 11/2007 | Wyrick ............... 604/117 |
| 2002/0042589 A1 | * | 4/2002 | Marsoner ............... 604/46 |
| 2004/0116847 A1 | * | 6/2004 | Wall ............... 604/93.01 |
| 2004/0182471 A1 | * | 9/2004 | Hansen ............... A61J 1/2089 141/23 |
| 2005/0187519 A1 | | 8/2005 | Harris |
| 2007/0016149 A1 | | 1/2007 | Hunn |
| 2007/0016150 A1 | | 1/2007 | Barkhahn |
| 2007/0191780 A1 | * | 8/2007 | Modi ............... 604/187 |
| 2010/0137831 A1 | * | 6/2010 | Tsals ............... A61M 5/3243 604/506 |
| 2012/0136300 A1 | * | 5/2012 | Schoonmaker et al. ...... 604/117 |

FOREIGN PATENT DOCUMENTS

| | | | |
|---|---|---|---|
| EP | 0 904 790 A2 | | 3/1999 |
| GB | 770341 | * | 3/1957 |
| JP | 9-10308 A | | 1/1997 |
| JP | 9-504974 A | | 5/1997 |
| JP | 9-285539 A | | 11/1997 |
| JP | 2001-9032 A | | 1/2001 |
| JP | 2005-21291 A | | 1/2005 |
| JP | 2005-538773 A | | 12/2005 |
| JP | 2009-526575 A | | 7/2009 |
| WO | WO 95/13833 | | 5/1995 |
| WO | WO 02/04053 A1 | | 1/2002 |
| WO | WO 2008/083209 | * | 7/2008 |
| WO | WO 2008/083209 A2 | | 7/2008 |
| WO | WO 2009/098502 A2 | | 8/2009 |

OTHER PUBLICATIONS

Supplementary Partial European Search Report, Mailed Jul. 30, 2014, 9 pages.

* cited by examiner

SELF-INJECTION DEVICE

FIELD OF THE INVENTION

The present invention relates to a self-injection device. More particularly, the present invention relates to a self-injection device having a compressible reservoir. Still more particularly, the present invention relates to a self-injection device having an adjustable injection depth to allow an intradermal, junctional or subcutaneous injection, as well as allowing the self-injection device to be filled with a medicament. Still more particularly, the self-injection device has a passive safety mechanism to prevent accidental needle sticks.

BACKGROUND OF THE INVENTION

Syringes are used to inject medicaments into tissue areas, such as the subcutaneous tissue layer, the intradermal tissue layer or the junctional area between the intradermal and subcutaneous tissue layers. However, existing syringes are only able to deliver medicament to one of these tissue layers. Thus, a separate inventory of syringes is required for delivering medicament to each of the intradermal, junctional and subcutaneous tissue layers, thereby increasing inventory and manufacturing costs.

Accordingly, a need exists for a syringe adapted to deliver medicament to any of the intradermal, subcutaneous and junctional tissue layers.

Additionally, a need exists for incorporation of safety mechanisms into such a device to prevent the spread of bacterial and viral pathogens via a needle stick or other accident.

SUMMARY OF THE INVENTION

The self-injection device according to an exemplary embodiment of the present invention has an adjustable injection depth, thereby allowing intradermal, junctional or subcutaneous injections with the same self-injection device.

In accordance with an exemplary embodiment of the present invention, a self-injection device includes a housing, and a needle connected to the housing. The needle is movable between a first position in which a proximal end of the needle is disposed within the housing and a second position in which the proximal end of the needle is disposed outside of the housing. A compressible reservoir is connected to the housing and in fluid communication with the needle such that compressing the reservoir delivers medicament from the reservoir to the needle and moves the needle from the first position to the second position.

In accordance with another exemplary embodiment of the present invention, a self-injection device includes a housing, and a needle connected to the housing. The needle is movable between a first position in which the needle is disposed entirely within the housing and a second position in which a proximal end of the needle is disposed outside of the housing. A platform is disposed within the housing about which the housing is rotatable between a plurality of positions. Each of the positions corresponds to a different distance the needle is moved to the second position during an injection.

In accordance with another exemplary embodiment of the present invention, a method of administering a medicament with an injection device is provided. The device is placed on the site where the medicament is to be delivered. A reservoir, which is connected to the housing and to a needle disposed in the housing, is depressed to inject the needle into the site and to deliver the medicament stored in the reservoir from the reservoir, through the needle and into the site. The desired injection depth is selected by rotating an upper housing of the housing relative to a lower housing.

BRIEF DESCRIPTION OF THE DRAWINGS

The above benefits and other advantages of the various embodiments of the present invention will be more apparent from the following detailed description of exemplary embodiments of the present invention and from the accompanying drawing figures, in which.

Throughout the drawings, like reference numbers will be understood to refer to like parts, components and structures.

DETAILED DESCRIPTION OF THE EXEMPLARY EMBODIMENT

Figure 2:
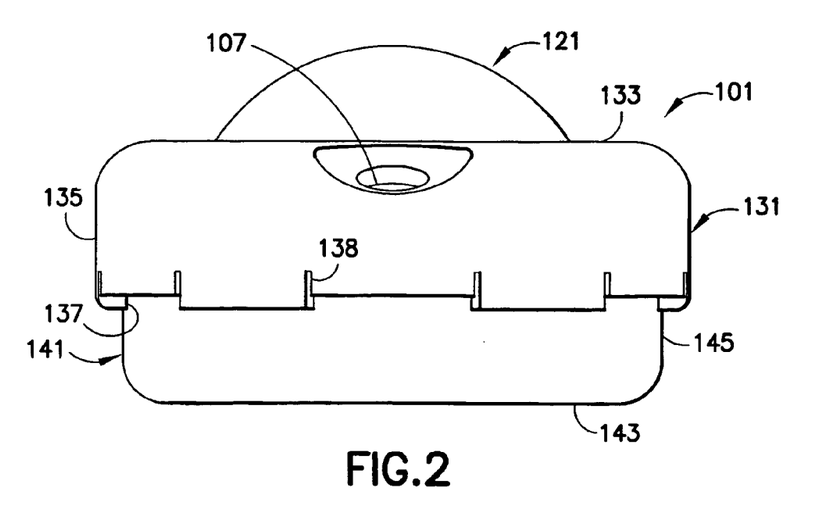
FIG. 2 is an elevational view of the self-injection device of FIG. 1.
Figure 3:
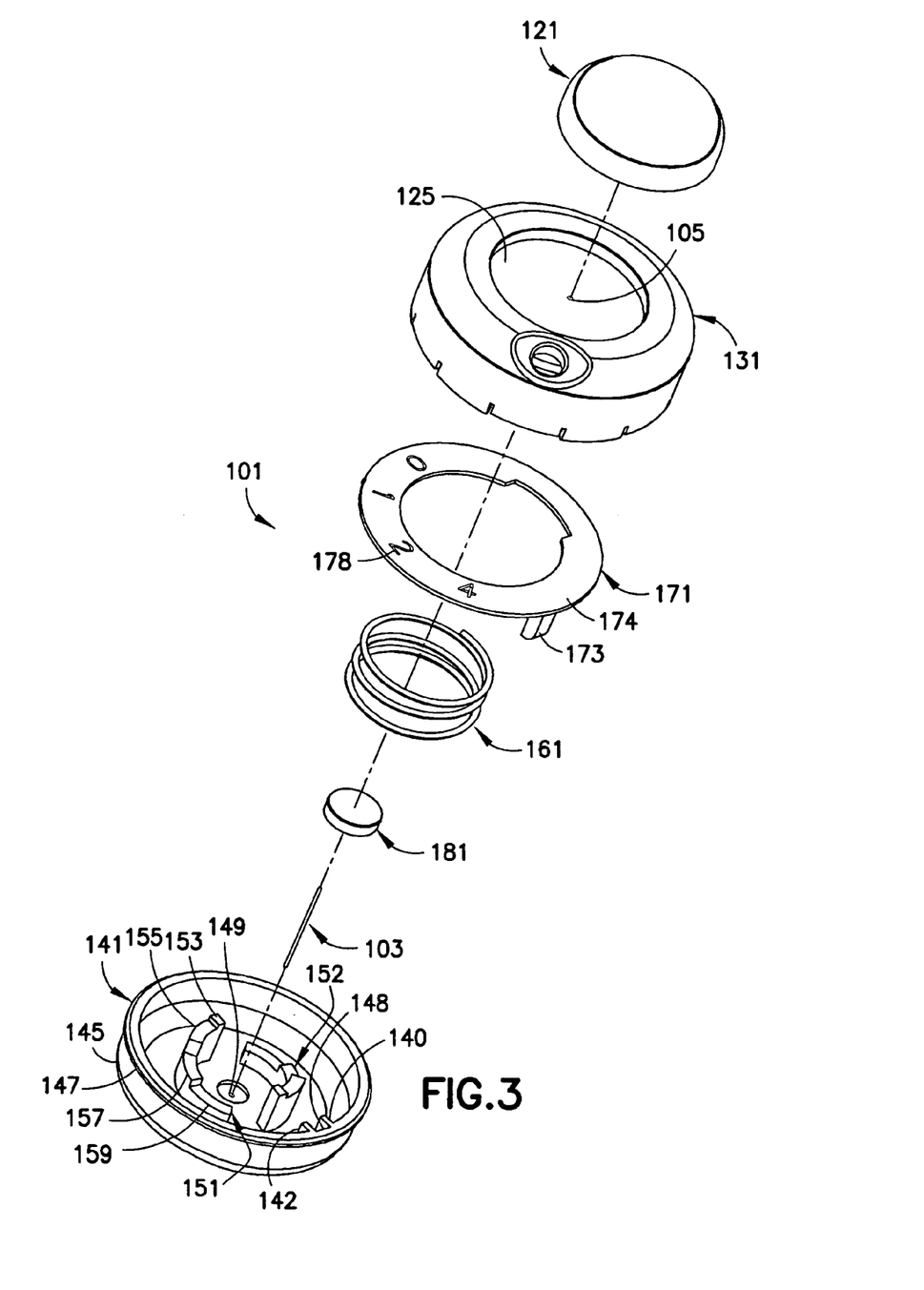
FIG. 3 is an exploded perspective view of the self-injection device of FIG. 1.
Figure 4:
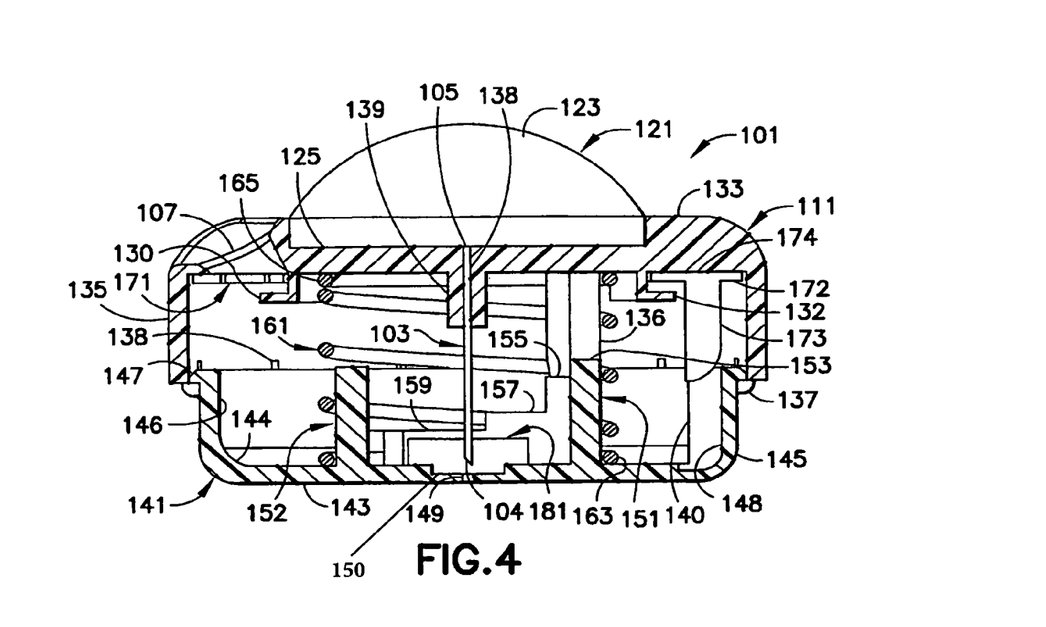
FIG. 4 is an elevational view in partial cross-section of the self-injection device of FIG. 1.
Figure 5:
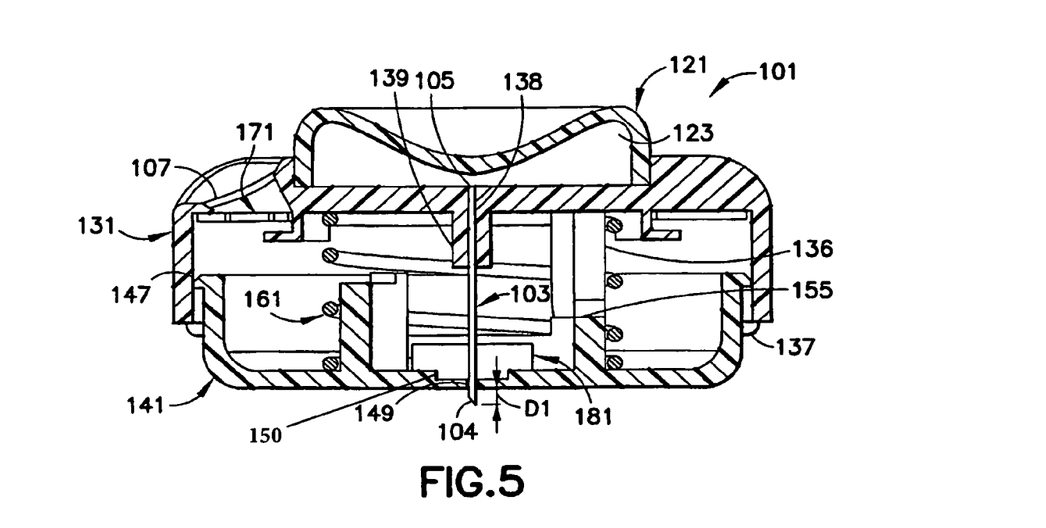
FIG. 5 is an elevational view in cross-section of the self-injection device set for an intradermal injection.
Figure 6:
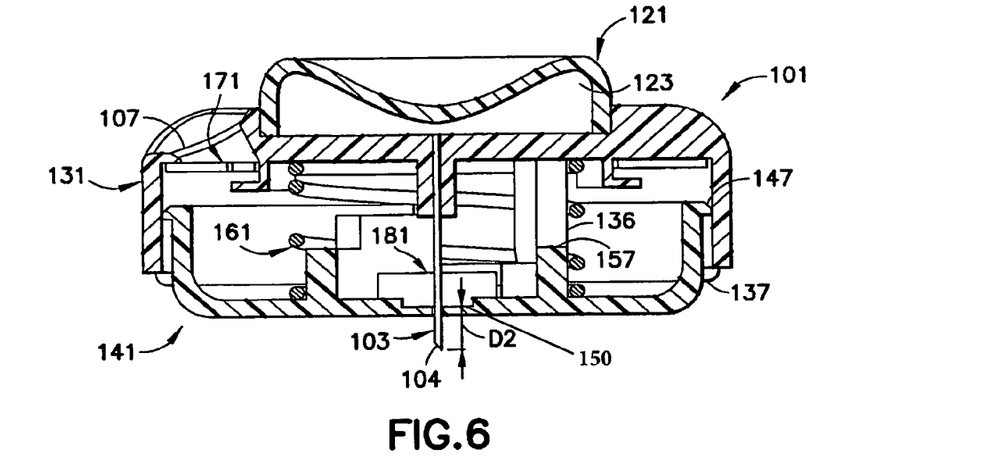
FIG. 6 is an elevational view in cross-section of the self-injection device set for a junctional injection.
Figure 7:
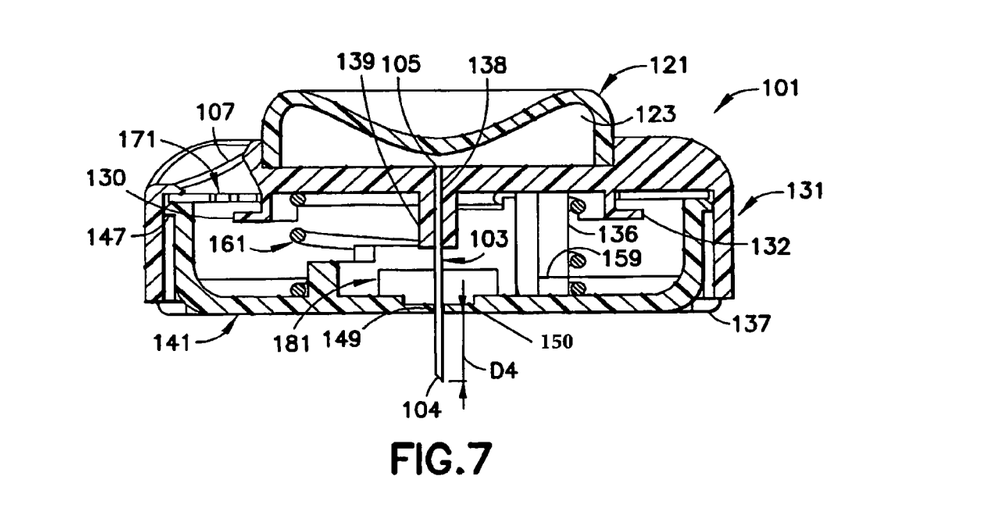
FIG. 7 is an elevational view in cross-section of the self-injection device set for a subcutaneous injection.

A self-injection device 101 according to an exemplary embodiment of the present invention, as shown in FIGS. 1-9, includes a housing 111, a needle 103 connected to the housing, and a compressible reservoir 121 connected to the housing. The needle 103 is movable between a first position as shown in FIG. 4, in which the proximal end 104 of the needle is disposed within the housing 111, and a second position in which a proximal end 104 of the needle is disposed outside of the housing as shown in FIGS. 5-7. The reservoir 121 is in fluid communication with the needle 103 such that compressing the reservoir delivers medicament from the reservoir to the needle and moves the needle from the first position to the second position.

The housing 111 includes an upper housing 131 and a lower housing 141, as shown in FIGS. 3-4. The housing is made of a suitable plastic material, such as polypropylene.

The upper housing 131 has a base 133 and a wall 135 extending substantially perpendicularly from an outer edge thereof. A free end of the wall 135 has a plurality of inwardly extending tabs 137. Cut-out portions 138 are formed in the wall 135 adjacent the tabs 137 to facilitate the flexibility of the tabs. A projection 139 extends outwardly from an inner surface 134 of the base 133 of the upper housing 131. An opening 138 extends through the entire length of the projection 139. A first tab (not shown) and a second tab 136 extend downwardly from the inner surface 134 and are diametrically opposed with respect to the projection 139. First and second flanges 130 and 132 extend downwardly from the inner surface 134 and are diametrically opposed with respect to the projection 139. Preferably, the first and second flanges 130 and 132 are substantially L-shaped and are disposed radially outwardly of the first and second tabs 136 and 138 relative to the projection 139. A window 107 is formed in the base 133 of the upper housing 131. The upper housing preferably has an outer diameter of approximately 31 millimeters.

The lower housing 141 has a base 143 and a wall 145 extending substantially perpendicularly from an outer edge thereof, as shown in FIGS. 2 and 4. A free end of the wall 145 has an outwardly extending lip 147. An opening 149 in a cavity 150 of the base 143 is adapted to allow a needle 103 to pass therethrough. A groove 148 is formed on an inner surface 146 of the wall 145, as shown in FIG. 3. The groove 148 is formed between first and second members 140 and 142. The distance from the outer surface of the base 143 of the lower housing 141 to the outer surface of the base 133 of the upper housing 131 is preferably approximately 15 millimeters. The distance from the outer surface of the base 143 of the lower housing 141 to the top of the uncompressed reservoir 121 is preferably approximately 21 millimeters.

An adhesive backing may be disposed on the outer surface of the base 143 of the lower housing 141 to substantially prevent movement of the self-injection device 101 when placed on a skin surface to perform an injection. The adhesive backing may also assist in immobilizing, fixing, stretching or spreading the skin to facilitate the injection.

A series 151 of steps 153, 155, 157 and 159 extend upwardly from an inner surface 144 of the base 143, as shown in FIG. 3. Preferably, there are four adjacent steps of decreasing height. The first step 153 is the highest step and is adapted to prevent downward movement of the top housing 131 and the needle 103. The second step 155 is adjacent the first step 153 and is adapted to allow movement of the needle 104 for an intradermal injection. The third step 157 is adjacent the second step 155 and is adapted to allow movement of the needle for a junctional injection. The fourth step 159 is adjacent the third step 157 and is adapted to allow movement of the needle for a subcutaneous injection. Preferably, a second set of identical steps are diametrically opposed from the first series of steps 151 with regard to the opening 149 in the base 145. Although this exemplary embodiment provides three different injection depths, the present invention is not limited to such embodiment and fewer or more injection depths are within the scope of the invention.

The skin is made up of three layers: epidermis, dermis and subcutaneous layers. The epidermis is the outermost layer of the skin, with the dermis layer underlying the epidermis, and the subcutaneous layer underlying the dermis. An intradermal injection is made in the dermis layer, and requires an injection depth of approximately 1 mm. A junctional injection is made in the junction between the dermis and the subcutaneous layers, and requires an injection depth of approximately 2 mm. A subcutaneous injection is made in the subcutaneous layer, and requires an injection depth of approximately 4 mm.

A spring 161 is disposed inside the housing 111, as shown in FIGS. 3 and 4. A first end 163 of the spring 161 abuts the inner surface 144 of the base 143 of the lower housing 141. A second end 165 of the spring 161 abuts the inner surface 134 of the base 133 of the upper housing 131. Preferably, the spring 161 is disposed radially outwardly of the steps 153, 155, 157 and 159 of the lower housing 141 and the tabs 136 of the upper housing 131, as shown in FIG. 4.

Figure 8:
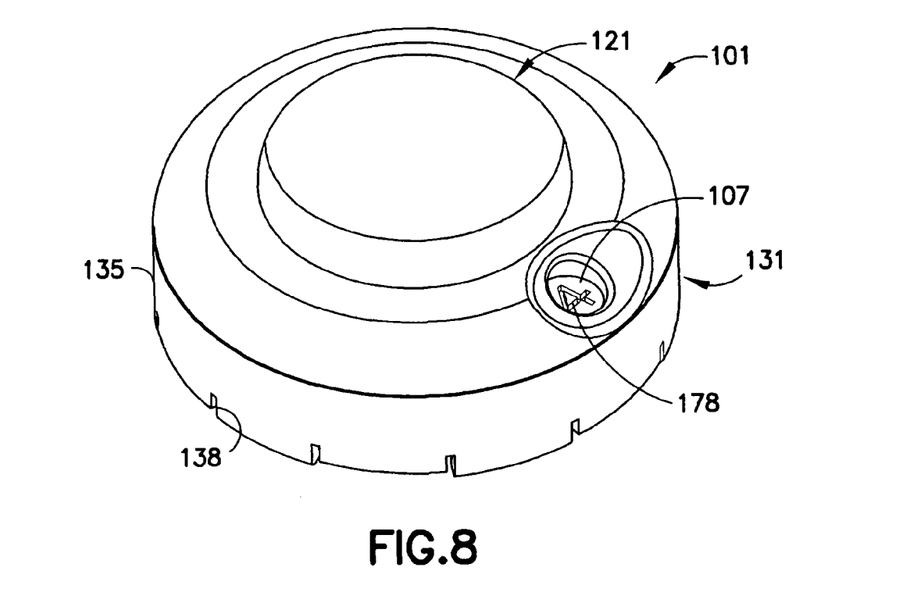
FIG. 8 is a perspective view from above of the self-injection device of FIG. 7.

A platform 171 is disposed adjacent the inner surface 134 of the base 133 of the upper housing and is secured thereto by the first and second flanges 130 and 132, as shown in FIGS. 3 and 4. A stop 173 extends outwardly from a lower surface 172 of the platform 171. The stop 173 is received by the groove 148 formed on an inner surface of the wall 145 of the lower housing 141. The stop 173 is received in the groove 148, thereby allowing the upper housing 131 to rotate relative to the platform 171, which is prevented from rotating by the stop 173 disposed in the groove 173 of the lower housing 143. A plurality of position indicators 178 are marked on an upper surface 174 of the platform 171 and are visible through the window 107 in the upper housing 131, as shown in FIGS. 3 and 8.

Figure 1:
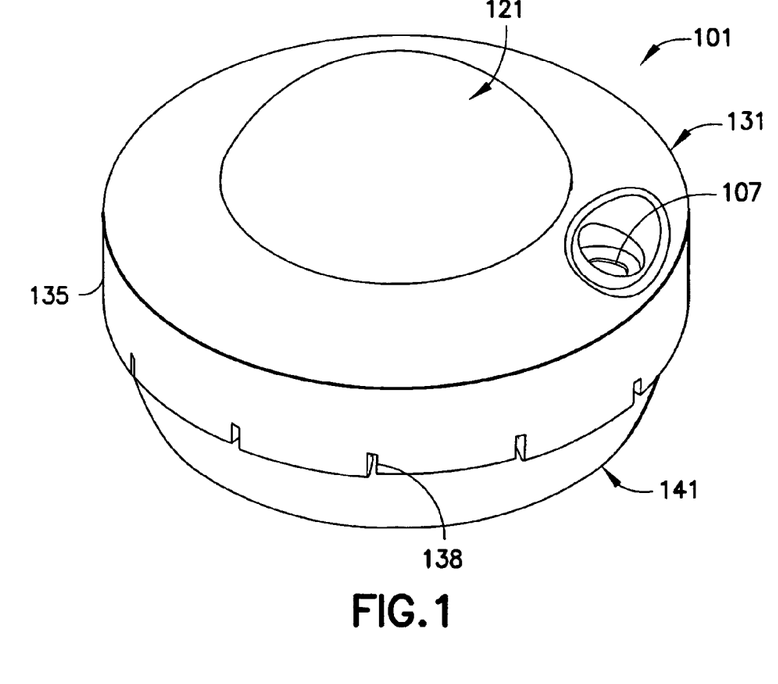
FIG. 1 is a perspective view of a self-injection device according to an exemplary embodiment of the present invention.

A compressible reservoir 121 is connected to the upper housing 131, as shown in FIGS. 1-3. A volume 123 is formed within the reservoir 121 defined by the reservoir 121 and the upper housing 131 in which medicament is stored. A recess 125 is formed in the upper surface 133 of the upper housing 131 to receive the compressible reservoir 121. The compressible reservoir 121 may be secured to the upper housing 131 in any suitable manner, such as by providing an outwardly extending flange on the compressible reservoir 121 that is received within a groove formed in the recess 125, by an adhesive that secures the compressible reservoir 121 in the recess 125, or by an interference fit between the compressible reservoir 121 and the recess 125. The compressible reservoir 121 is made of a suitable flexible plastic or elastomeric material, such as nylon or silicone rubber.

The needle 103 is fixedly connected to the base 133 of the upper housing 131, as shown in FIGS. 4-7. The needle 103 has a distal end 105 flush with the opening 138 in the recess 125 of the upper housing 131. The proximal end 104 of the needle 103 is disposed in the housing 111 when the upper housing 131 is in its initial position, as shown in FIG. 3. Preferably, the proximal end 104 of the needle 103 is disposed within a resilient septum 181 when the upper housing 131 is in its initial position.

The septum 181 is connected to an inner surface 144 and to the cavity 150 of the base 143 of the lower housing 141, as shown in FIG. 4, and covers the opening 149 in the lower housing. The septum 181 is preferably solid and elastic, and allows the needle 103 to pass therethrough when the needle is moved during an injection. The septum 181 acts as a shield and seal by covering the proximal end 104 of the needle 103, thereby preventing accidental needle sticks and sealing the opening 149. The septum is made of an appropriate elastomeric material, such as silicone rubber.

The self-injection device 101 may be pre-filled or filled by the user. The procedure for filling the self-injection device 101 with medicament is substantially similar to injecting medicament into a site, and is described hereafter.

The self-injection device is shown in the locked position in FIG. 4. The tabs 136 abut the first step 153, thereby preventing downward movement of the upper housing 131 relative to the lower housing 141. The proximal end 104 of the needle 103 is disposed within the housing 111, and preferably within the septum 181. An indicator on the platform 171 is visible through the window 107 of the upper housing to indicate that the self-injection device is in the locked position, such as the numeral "0" (FIG. 3) to indicate that the needle is movable 0 millimeters in this setting, i.e., not movable.

The inner diameter of the upper housing 131 is larger then the outer diameter of the lower housing 141, as shown in FIG. 4. Thus, the upper housing 131 is movable downwardly over the lower housing 141, as shown in FIGS. 5-9. The tabs 137 of the upper housing 131 prevent the upper housing from being separated from the lower housing 141 by engaging the outwardly extending lip 147 when the spring 161 expands after an injection. The slots 138 in the upper housing provide flexibility to the tabs 137 such that the tabs may be flexed over the lip 147 during initial assembly of the self-injection device 101.

The self-injection device is shown in a position corresponding to an intradermal injection in FIG. 5. The upper housing 131 is rotated relative to the platform 171 such that the indicator visible through the window 107 indicates that the self-injection device is in the intradermal position. The indicator may be the numeral "1" (FIG. 3) to indicate that the needle 103 is movable one millimeter, which corresponds to the depth required for an intradermal injection. The stop 173 of the platform 171 is disposed within the groove 148 of the lower housing 141, thereby preventing rotation of the platform 171 and lower housing 141 when the upper housing 131 is rotated. To perform the intradermal injection, the reservoir is depressed, thereby moving the upper housing 131 downwardly until the tabs 136 abut the second step 155. The spring 161 is compressed between the upper and lower housings 131 and 141, respectively. This results in approximately one millimeter of travel for the needle 103 beyond the base 143 of the lower housing 141, as shown by the distance D1 of FIG. 5. Preferably, the distance from the outer surface of the base 143 of the lower housing 141 to the outer surface of the base 133 of the upper housing 131 when the reservoir 121 is compressed for an intradermal injection is preferably approximately 13 millimeters.

The needle 103 is fixed to and moves with the upper housing 131. The proximal end 104 of the needle 103 passes through the septum 181 and through the opening 149 in the cavity 150 of the base 143 of the lower housing 141. Medicament stored in the cavity 123 of the reservoir 121 enters the distal end 105 of the needle 103, travels through the needle 103 and into the injection site. Upon releasing the reservoir 123, the compressed spring 161 expands. This action withdraws the needle 103 from the injection site and through the opening 149 such that the proximal end 104 of the needle 103 is again disposed within the septum 181. Preferably, the self-injection device 101 is discarded after being used for an injection. The proximal end 104 of the needle 103 being disposed in the septum 181 prevents an accidental needle stick following the injection.

Figure 9:
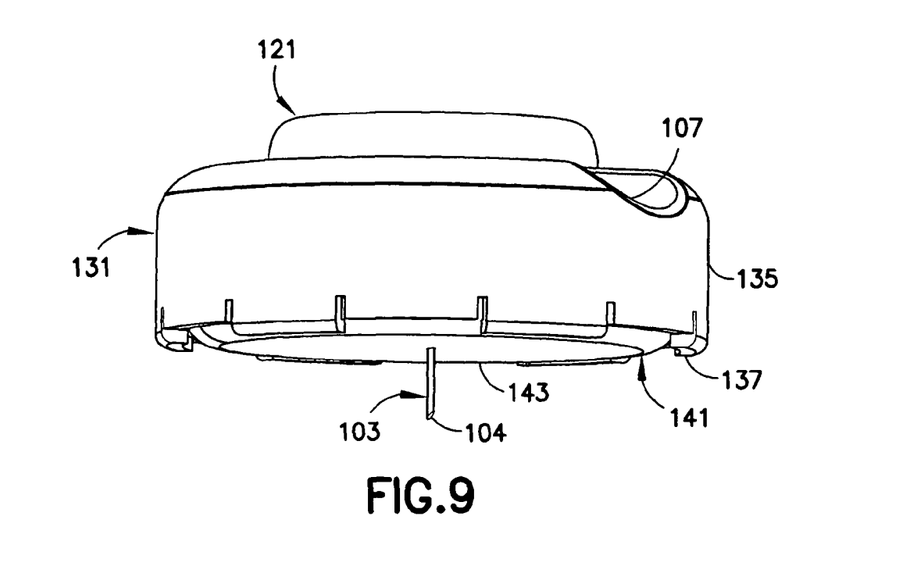
FIG. 9 is a perspective view from below of the self-injection device of FIG. 8.

As described in the preceding paragraph, the upper housing 131 is rotatable to positions corresponding to a junctional injection (FIG. 6) and a subcutaneous injection (FIGS. 7-9). In the junctional injection position, the platform indicator may be the numeral "2" (FIG. 3) to indicate needle travel of approximately two millimeters beyond the base of the lower housing, which corresponds to the distance required for a junctional injection. The tabs 136 of the upper housing 131 abut the third step 155 when the reservoir 121 is depressed to limit the needle 103 travel to approximately two millimeters, as shown by the distance D2 of FIG. 6. Preferably, the distance from the outer surface of the base 143 of the lower housing 141 to the outer surface of the base 133 of the upper housing 131 when the reservoir 121 is compressed for a junctional injection is preferably approximately 12 millimeters.

In the subcutaneous injection position, the platform indicator may be the numeral "4" (FIG. 3) to indicate needle travel of approximately four millimeters beyond the base of the lower housing, which corresponds to the distance required for a subcutaneous injection, as shown by the distance D4 of FIG. 7. The tabs 136 of the upper housing 131 abut the fourth step 155 when the reservoir 121 is depressed to limit the needle 103 travel to approximately four millimeters. Preferably, the distance from the outer surface of the base 143 of the lower housing 141 to the outer surface of the base 133 of the upper housing 131 when the reservoir 121 is compressed for a subcutaneous injection is preferably approximately 10 millimeters. The remaining process for performing an injection is substantially similar to the process described above for the intradermal injection.

To fill an empty reservoir, the process is similar to performing a subcutaneous injection. The upper housing 131 is rotated to the position corresponding to the subcutaneous injection, as shown in FIGS. 7-9. The self-injection device 101 is disposed adjacent a vial containing the desired medicament. The reservoir 131 is depressed, such that the proximal end 104 of the needle 103 enters the medicament. Releasing the reservoir 131 draws medicament up through the needle 103 and into the cavity 123 of the reservoir 121. The upper housing 131 is then rotated to the locked position, as shown in FIG. 4, to prevent accidental movement of the needle 103. Alternatively, the self-injection device 101 may be provided to a user in a pre-filled condition.

The compact size of the self-injection device 101 makes it user-friendly, particularly in view of being operable with one hand. Each component of the self-injection device 101 is multifunctional, thereby reducing the number of parts required for assembly. Furthermore, as noted above, after performing an injection the upper housing 131 is rotated back to the lock position, thereby preventing accidental needle sticks and converting the self-injection device 101 into its own self-contained "sharps collector."

Furthermore, the self-injection device 101 incorporates a safety mechanism to prevent the spread of bacterial and viral pathogens via a needle stick or other accident. As noted above, upon release of the reservoir 121 the needle 103 is withdrawn back into the housing 111, as shown in FIG. 4. The proximal end 104 of the needle 103 is disposed within the septum 181, thereby preventing an accidental needle stick or other accident following an injection. The needle 103 is withdrawn passively, such that a user does not need to remember to actively retract the needle, thereby providing a safe self-injection device 101.

Figure 10:
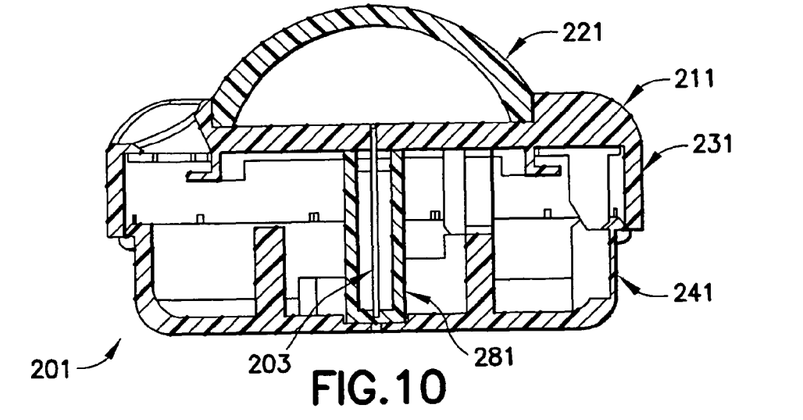
FIG. 10 is an elevational view in partial cross-section of another exemplary embodiment of a self-injection device having an elongated septum.
Figure 11:
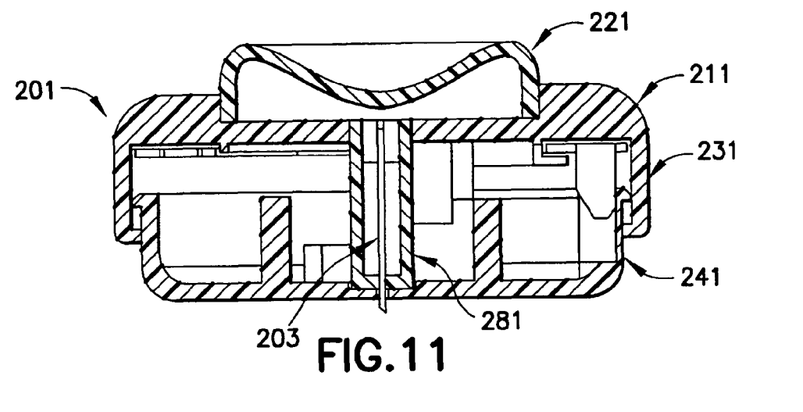
FIG. 11 is an elevational view in partial cross-section of the self-injection device of FIG. 10 in which the reservoir is depressed.

In another exemplary embodiment of the present invention, as shown in FIGS. 10 and 11, a self-injection device 201 is substantially similar to the self-injection device 101. An elongated hollow, septum 281 is disposed within the housing 211. Upon compression of the reservoir 221, as shown in FIG. 11, the upper housing 231 is moved downwardly relative to the lower housing 241, thereby compressing the resilient septum 281. The needle 203 is rigidly fixed to the upper housing 231 such that the needle passes through the septum 281. Upon releasing the reservoir 221, the elasticity of the septum 281 returns the upper housing 231 to its initial position, as shown in FIG. 10. The proximal end of the needle 203 is also passively withdrawn into the housing 211, thereby providing a safe self-injection device 201 that prevents needle sticks and other accidents.

Figure 12:
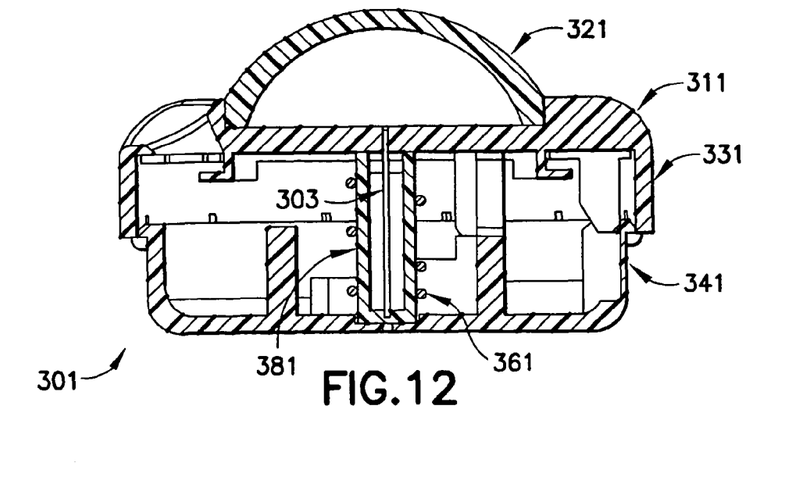
FIG. 12 is an elevational view in partial cross-section of another exemplary embodiment of a self-injection device having an elongated septum and a spring.

In another exemplary embodiment, as shown in FIG. 12, a self-injection device 201 is substantially similar to the self-injection device 101. An elongated hollow, septum 381 is disposed within the housing 311. A spring 361 surrounds the septum 381 to facilitate returning the resilient septum to its initial position, as shown in FIG. 12, after being compressed. The upper housing 331 moves downwardly relative to the lower housing 341 when the reservoir 321 is compressed. The needle 303 is rigidly fixed to the upper housing 331 such that the needle passes through the septum 381. Upon releasing the reservoir 321, the elasticity of the septum 281 in combination with the spring 361 returns the upper housing 331 to its initial position, as shown in FIG. 12. The proximal end of the needle 303 is also passively withdrawn into the housing 311, thereby providing a safe self-injection device 301 that prevents needle sticks and other accidents.

A self-injection device according to exemplary embodiments of the present invention provides a safe and user-friendly push-button self-injection device, which allows for injection of a medicament, such as a vaccine or insulin. The self-injection device includes passive retraction of the needle to prevent the spread of bacterial and viral pathogens via a needle stick or other accident. The desired injection depth is selected and the self-injection device is placed on the patient's skin. The compressible reservoir is depressed, thereby injecting the needle into the skin and administering the medicament. Alternatively, a reservoir fill mode may be selected, and the self-injection device is placed over a vial containing a medicament to draw the medicament into the compressible reservoir. Releasing the compressible reservoir automatically withdraws the needle, thereby providing a safe self-injection device.

While exemplary embodiments have been chosen to illustrate the invention, it will be understood by those skilled in the art that various changes and modifications may be made therein without departing from the scope of the invention as defined in the appended claims and their equivalents.

The invention claimed is:

1. A self-injection device for delivering a medicament, comprising:
    a housing having a first housing part and a second housing part engaged with and selectively movable with respect to each other between a plurality of housing positions, said second housing part movable within said first housing part;
    one of said first and second housing parts having a needle movable between a first needle position in which a proximal end of the needle is disposed within said housing and a second needle position in which the proximal end of said needle is disposed outside of said housing; and
    a compressible reservoir disposed external to said housing and in fluid communication with said needle, compression of said reservoir automatically causing (1) said reservoir to deform to expel a medicament and (2) said needle to move from said first needle position to said second needle position,
    wherein each of said housing positions corresponds to a different distance said needle moves between said first and second needle positions.

2. The self-injection device of claim 1, wherein said first housing part and said second housing part are rotatable with respect to each other between said plurality of housing positions.

3. The self-injection device of claim 2, wherein said plurality of housing positions defines a plurality of depths to which the proximal end of said needle travels in a patient's skin, each of said plurality of said depths corresponding to one of intradermal, junctional or subcutaneous injections.

4. The self-injection device of claim 3, wherein said plurality of housing positions are defined by a tab defined on one of said first and second housing parts, and by a step defined on the other one of said first and second housing parts.

5. The self-injection device of claim 4, wherein said tab and said step comprise one of at least four steps including, a first step preventing movement of said first and second housing parts with respect to each other when said reservoir is compressed, a second step limiting movement of said needle to a depth corresponding to an intradermal injection, a third step limiting movement of said needle to a depth corresponding to a junctional injection, and a fourth step limiting movement of said needle to a depth corresponding to a subcutaneous injection.

6. The self-injection device of claim 1, further comprising an elastic septum disposed in a cavity defined in said second housing part, at least a portion of said needle being disposed in said septum.

7. The self-injection device of claim 6, further comprising an adhesive on said second housing part to secure said device to a patient's skin during an injection.

8. The self-injection device of claim 1, further comprising biasing means normally biasing said first and second housing parts away from each other.

9. The self-injection device of claim 1, wherein the reservoir extends outwardly from the housing.

10. The self-injection device of claim 1, wherein the reservoir is a push-button directly contacted by the user during an injection.

11. The self-injection device of claim 1, wherein said reservoir and said needle are connected to said first housing part and depression of said reservoir moves said needle through said second housing part.

12. A self-injection device for delivering a medicament, comprising:
    a housing having a first housing part and a second housing part engaged with and selectively movable with respect to each other between a plurality of housing positions, said second housing part movable within said first housing part;
    one of said first and second housing parts having a needle movable between a first needle position in which the needle is disposed entirely within said housing and a second needle position in which a proximal end of said needle is disposed outside of said housing;
    a compressible reservoir disposed external to said housing and in fluid communication with said needle, compression of said reservoir automatically causing (1) said reservoir to deform to expel the medicament and (2) said needle to move from said first needle position to said second needle position; and
    said first housing part and said second housing part being rotatable with respect to each other between said plurality of housing positions, each of said housing positions setting a different distance for movement of said needle between said first and second needle positions.

13. The self-injection device according to claim 12, wherein said plurality of housing positions defines a plurality of depths to which said proximal end of said needle travels in a patient's skin, each of said plurality of housing positions corresponding to injection depths for intradermal, junctional and subcutaneous injections.

14. The self-injection device of claim 13, further comprising biasing means between said first and second housing parts, said biasing means normally biasing said first and second housing parts away from each other.

15. The self-injection device of claim 12, wherein said plurality of housing positions are defined by a tab on one of said first and second housing parts, and by a step on the other one of said first and second housing parts.

16. The self-injection device of claim 15, wherein said tab and said step comprise one of at least four steps, including a first step preventing movement of said first and second housing parts with respect to each other when said reservoir is compressed, a second step limiting movement of said needle to a depth corresponding to an intradermal injection, a third step limiting movement of said needle to a depth corresponding to a junctional injection, and a fourth step limiting movement of said needle to a depth corresponding to a subcutaneous injection.

17. The self-injection device of claim 12, further comprising an elastic septum disposed in a cavity defined in said second housing part, at least a portion of said needle being disposed in said septum.

18. A method of administering a medicament with an injection device, comprising the steps of:
   placing the device on a site where the medicament is to be delivered;
   rotating a first housing part of a housing relative to a second housing part of the housing between a plurality of positions to select a desired injection depth, each of the plurality of positions corresponding to a different injection depth; and
   depressing a reservoir connected to the housing and disposed external to the housing, thereby deforming the reservoir and moving a needle connected to the housing from a first position within the housing to a second position to inject the needle into the site and to cause the medicament contained within the reservoir to be expelled from the reservoir, through the needle and into the site.

19. The method of claim 18, further comprising the step of filling the reservoir prior to delivering the medicament by disposing the device on a medicament container and depressing the reservoir to withdraw the medicament from the container and into the reservoir.

20. The method of claim 18, further comprising the step of releasing the reservoir to passively withdraw the needle such that a proximal end of the needle is disposed within the housing upon releasing the reservoir without manual manipulation of the needle, thereby preventing an accidental needle stick.

* * * * *